(12) United States Patent
Bigge et al.

(10) Patent No.: US 6,696,474 B2
(45) Date of Patent: Feb. 24, 2004

(54) ANTIDIABETIC AGENTS

(75) Inventors: Christopher F. Bigge, Ann Arbor, MI (US); Robert P. Schaum, Ann Arbor, MI (US)

(73) Assignee: Warner Lambert Co. LLC., Ann Arbor, MI (US)

( * ) Notice: Subject to any disclaimer, the term of this patent is extended or adjusted under 35 U.S.C. 154(b) by 0 days.

(21) Appl. No.: 10/390,466

(22) Filed: Mar. 17, 2003

(65) Prior Publication Data

US 2003/0220381 A1 Nov. 27, 2003

Related U.S. Application Data

(60) Provisional application No. 60/369,787, filed on Apr. 3, 2002.

(51) Int. Cl.[7] .................. A61K 31/422; A61P 3/10; C07D 413/06
(52) U.S. Cl. ........................... 514/374; 548/236
(58) Field of Search .................. 548/236; 514/374

(56) References Cited

U.S. PATENT DOCUMENTS 6,248,897 B1 * 6/2001 Ando et al. .................. 548/236

FOREIGN PATENT DOCUMENTS

EP 1108713 6/2001

* cited by examiner

*Primary Examiner*—Robert W. Ramsuer
(74) *Attorney, Agent, or Firm*—Elsa Djuardi; Bryan C. Zielinski; Peter C. Richardson

(57) ABSTRACT

Compounds of formula I:

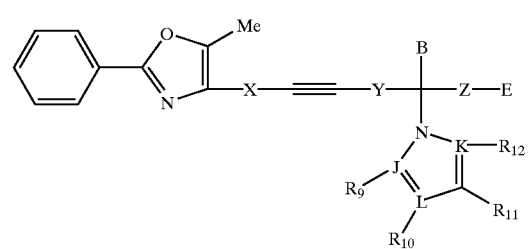

wherein X, Y, B, E, J, K, L, Z, and $R_9$–$R_{12}$ have any of the meanings described herein, their pharmaceutically acceptable salts, lower blood glucose levels and are useful for treating diseases in mammals such as Non-Insulin Dependent Diabetes Mellitus. Also disclosed are pharmaceutical compositions, processes for preparing compounds of formula (I) and intermediates useful for preparing compounds of formula I.

15 Claims, No Drawings

ANTIDIABETIC AGENTS

CROSS REFERENCE TO RELATED APPLICATIONS

This application claims benefit of priority from U.S. Provisional Application Ser. No. 60/369,787 filed on Apr. 3, 2002.

FIELD OF THE INVENTION

The present invention relates to compounds that are useful as antidiabetic agents.

BACKGROUND OF THE INVENTION

Type II diabetes, or non-insulin dependent diabetes (NIDDM) is a significant healthcare problem whose incidence is on the rise. Between 1990 and 1998, the prevalence of NIDDM in the United States increased by 33 percent, to about 13 million persons. An additional 5 million persons are presumed to have undiagnosed NIDDM, while another 14 million persons have impaired glucose tolerance. Direct medical costs associated with diabetes were $44 billion in 1997, due mainly to hyperglycemia-related diabetic complications, including diabetic angiopathy, atherosclerosis, diabetic nephropathy, diabetic neuropathy, and diabetic ocular complications such as retinopathy, cataract formation, and glaucoma.

NIDDM is one of a number of disease states associated with the phenomenon of insulin resistance. Insulin resistance is defined as the reduced sensitivity to the actions of insulin in the whole body or individual tissues, such as skeletal muscle tissue, myocardial tissue, fat tissue or liver tissue. Insulin resistance occurs in many individuals with or without diabetes mellitus. Insulin resistance syndrome (hereinafter IRS) refers to the cluster of manifestations that include insulin resistance; hyperinsulinemia; non insulin dependent diabetes mellitus (NIDDM); arterial hypertension; central (visceral) obesity; and dyslipidemia.

The primary goal of IRS therapy and thus diabetes therapy is to lower blood glucose levels so as to prevent acute and long-term disease complications. For some persons, modified diet and increased exercise may be a successful therapeutic option for achieving the goal of glucose control. When modified diet and increased exercise are not successful, drug therapy using oral antidiabetic agents is initiated.

To date, a number of oral antidiabetic agents have been developed. For instance, sulfonylureas are generally used to stimulate insuln. The biguanide metformin is generally used to improve insulin sensitivity and to decrease hepatic glucose output. Acarbose is used to limit postprandial hyperglycemia, Thiazolidine 2,4 diones are used to enhance insulin action.

New drug therapies for the treatment of NIDDM have focused in part on the discovery of new Peroxisome Proliferator Activation Recpetor (PPAR) agonists. PPARs are members of the nuclear receptor superfamily of transcription factors that includes steroid, thyroid, and vitamin D receptors. PPARs play a role in controlling expression of proteins that regulate lipid metabolism. There are three PPAR subtypes: PPAR α, PPAR δ, and PPAR γ.

Each PPAR receptor shows a different pattern of tissue expression, and differences in activation by structurally diverse compounds. PPAR γ, for instance, is expressed most abundantly in adipose tissue and at lower levels in skeletal muscle, heart, liver, intestine, kidney, vascular endothelial and smooth muscle cells as well as macrophages. Two isoforms of PPAR γ exist, identified as $\gamma_1$ and $\gamma_2$, respectively. PPAR γ mediates adipocyte signalling, lipid storage, and fat metabolism. Evidence gathered to date support the conclusion that PPAR γ is the primary, and perhaps the only, molecular target mediating the insulin sensitizing action of one class of antidiabetic agents, the thiazolidine 2,4 diones.

In a monotherapeutic or combination therapy context, new and established oral antidiabetic agents are still considered to have non-uniform and even limited effectiveness. The effectiviness of oral antidiabetic therapies may be limited, in part, because of poor or limited glycemic control, or poor patient compliance due to unacceptable side effects. These side effects include edema weight gain, or even more serious complications. For instance, hypoglycemia is observed in some patients taking sulfonylureas. Metformin, a substituted biguanide, can cause diarrhea and gastrointestinal discomfort. Finally, edema, weight gain, and in some cases, hepatoxicity, have been linked to the administration of some thiazolidine 2,4 dione antidiabetic agents. Combination therapy using two or more of the above agents is common, but generally only leads to incremental improvements in glycemic control.

As a result, there is a need for oral antidiabetic agents that can be used alone or in combination, and that do not give rise to side effects such as fluid retention, peripheral edema, weight gain, or more severe complications.

SUMMARY OF THE INVENTION

These and other needs are addressed by the invention claimed by the instant application, which is directed to a compound of formula I

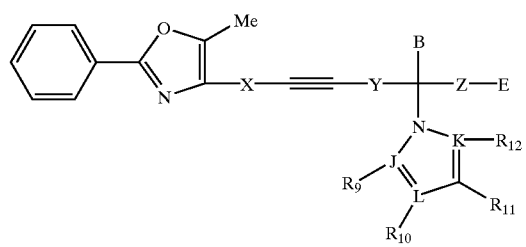

or a pharmaceutically acceptable salt thereof, wherein:

X is $(CR_1R_2)_x$ wherein x is 1, 2, 3, or X is
—$(CR_3R_4)$—CH=CH—,
—CH=CH—$(CR_3R_4)$—,
—$(CR_3R_4)$—C≡C—,
—C≡C—$(CR_3R_4)$—, wherein $R_1$–$R_4$ are each independently H, OH or $(C_1$–$C_6)$ alkoxy, or $R_3$ and $R_4$ taken together are =O, or $R_3$–$R_6$ are each independently or $(C_1$–$C_6)$alkyl;

Y and Z are $(CR_1R_2)_n$ and $(CR_3R_4)_m$ wherein m and n are each independently 0, 1, 2, or 3;

B is H or $(C_1$–$C_6)$alkyl;

E is $COR_5$, wherein $R_5$ is $(C_1$–$C_6)$alkyl, OH, $(C_1$–$C_6)$ alkoxy, $NR_6R_7$, wherein $R_6$ and $R_7$ are each independently H or $(C_1$–$C_6)$alkyl, or one of $R_6$ and $R_7$ is H or $(C_1$–$C_6)$alkyl and the other is $SO_2R_8$, wherein $R_8$ is H or $(C_1$–$C_6)$alkyl, or E is substituted heteroaryl or

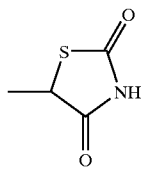

$R_9$–$R_{12}$ are each independently H, halo, aryl, ($C_1$–$C_6$) alkyl, halo($C_1$–$C_6$)alkyl, ($C_1$–$C_6$)alkanoyl, halo ($C_1$–$C_6$)alkanoyl, benzoyl, or halo($C_2$–$C_6$)alkanoyl; and one, two, or three of J, K, and L are N, provided that when J, K, or L are N, $R_9$, $R_{10}$, and $R_{12}$ are absent at that position.

What is also provided is a compound which is:

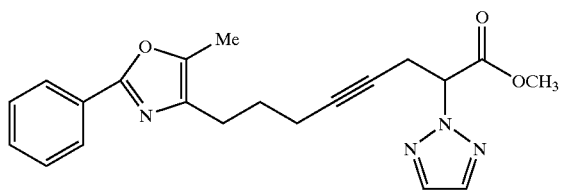

8-(5-Methyl-2-phenyl-oxazol-4-yl)-2-[1,2,3]triazol-2-yl-oct-4-ynoic acid methyl ester;

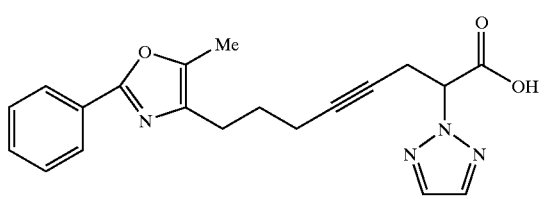

8-(5-Methyl-2-phenyl-oxazol-4-yl)-2-[1,2,3]triazol-2-yl-oct-4-ynoic acid;

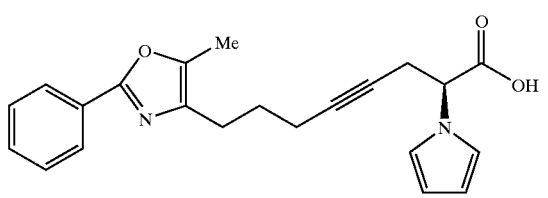

8-(5-Methyl-2-phenyl-oxazol-4-yl)-2-pyrrol-1-yl-oct-4-ynoic acid;

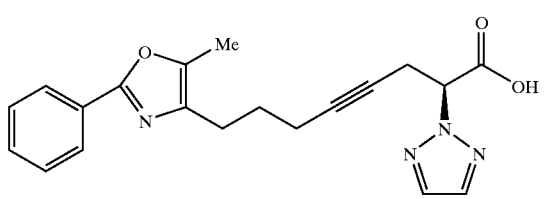

8-(5-Methyl-2-phenyl-oxazol-4-yl)-2-[1,2,3]triazol-2-yl-oct-4-ynoic acid;

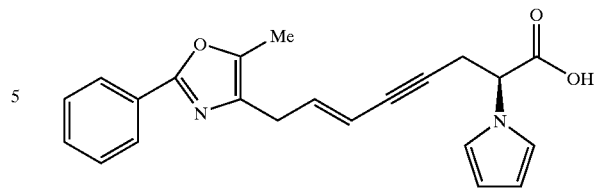

8-(5-Methyl-2-phenyl-oxazol-4-yl)-2-pyrrol-1-yl-oct-6-en-4-ynoic acid;

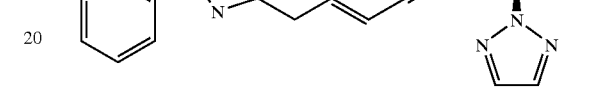

8-(5-Methyl-2-phenyl-oxazol-4-yl)-2-[1,2,3]triazol-2-yl-oct-6-en-4-ynoic acid;

6-Hydroxy-8-(5-methyl-2-phenyl-oxazol-4-yl)-2-pyrrol-1-yl-oct-4-ynoic acid;

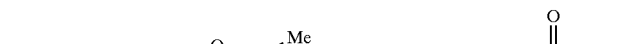

6-Hydroxy-8-(5-methyl-2-phenyl-oxazol-4-yl)-2-pyrrol-1-yl-oct-4-ynoic acid;

6-Methoxy-8-(5-methyl-2-phenyl-oxazol-4-yl)-2-pyrrol-1-yl-oct-4-ynoic acid;

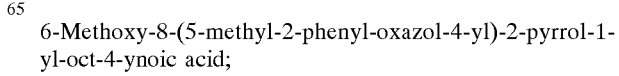

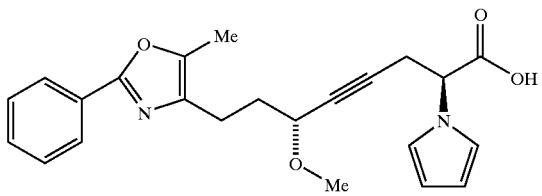

6-Methoxy-8-(5-methyl-2-phenyl-oxazol-4-yl)-2-pyrrol-1-yl-oct-4-ynoic acid;

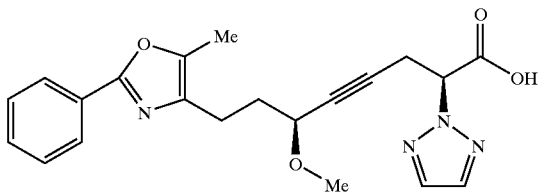

6-Methoxy-8-(5-methyl-2-phenyl-oxazol-4-yl)-2-[1,2,3]triazol-2-yl-oct-4-ynoic acid;

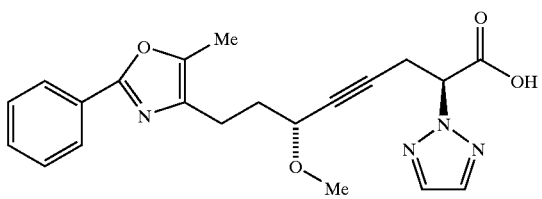

6-Methoxy-8-(5-methyl-2-phenyl-oxazol-4-yl)-2-[1,2,3]triazol-2-yl-oct-4-ynoic acid.

What is also provided is a pharmaceutical composition comprising a compound of formula I admixed with a carrier, diluent, or excipient.

What is also provided is a method of treating, preventing or controlling non-insulin dependent diabetes mellitus, obesity, hyperglycemia, hyperlipidemia, hypercholesteremia, atherosclerosis, hypertriglyceridemia, or hyperinsulinemia in a mammal comprising administering to the mammal in need thereof an effective amount of a compound of formula I.

What is also provided is a method of treating a patient suffering from abnormal insulin and/or evidence of glucose disorders associated with circulating glucocorticoids, growth hormone, catecholamines, glucagon, or parathyroid hormone, comprising administering to the patient a therapeutically effective amount of a compound of fomula I.

What is also provided is a method of reducing body weight in an obese mammal comprising administering to the mammal in need thereof an effective amount of a compound of formula I.

What is also provided is a method of preparing a compound of formula IA

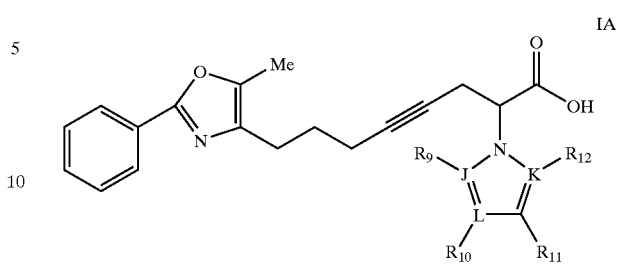

wherein $R_9$–$R_{12}$ are each independently H, halo, aryl, $(C_1$–$C_6)$alkyl, halo$(C_1$–$C_6)$alkyl, $(C_1$–$C_6)$alkanoyl, halo$(C_1$–$C_6)$alkanoyl, $(C_3$–$C_7)$cycloalkylcarbonyl, benzoyl, or halo$(C_2$–$C_6)$alkanoyl; and one, two, or three of J, K, and L are N, provided that when J, K, or L are N, $R_9$, $R_{10}$, and $R_{12}$ are absent at that position comprising:

(a) Conversion of the mesylate to the nitrile;
(b) Conversion of the nitrile to the primary alcohol;
(c) Conversion of the primary alcohol to the halide;
(d) Displacement of the halide with TMSacetylide to to form the TMS acetylene;
(e) Removal of the TMS group by hydrolysis;
(f) Treatment of the acetylene with base and reaction with formaldehyde to form the propargyl alcohol;
(g) Conversion of the primary alcohol to the Halde;
(h) Alkylation with "X" follwed by decarboxylation to form the ester; and
(i) Hydrolysis of the ester.

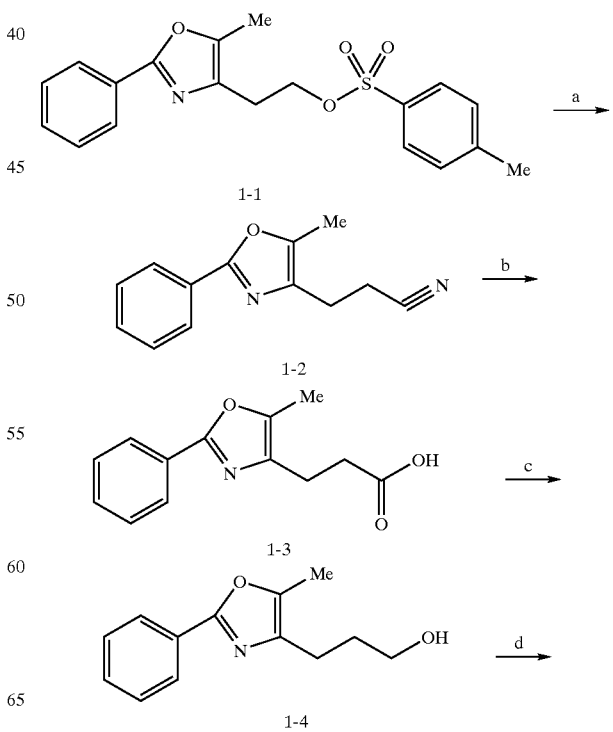

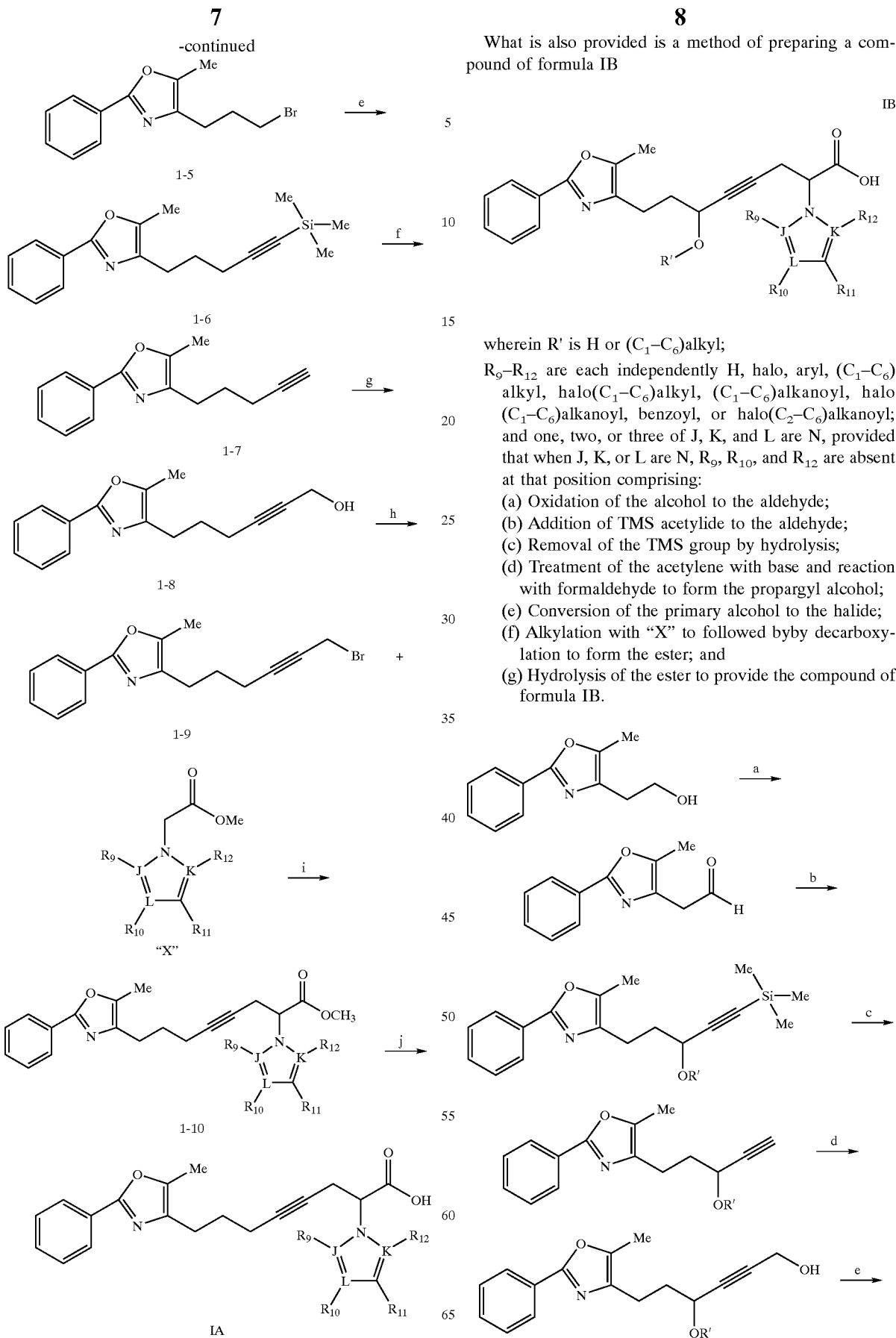

What is also provided is a method of preparing a compound of formula IB wherein R' is H or $(C_1-C_6)$alkyl;

$R_9-R_{12}$ are each independently H, halo, aryl, $(C_1-C_6)$ alkyl, halo$(C_1-C_6)$alkyl, $(C_1-C_6)$alkanoyl, halo $(C_1-C_6)$alkanoyl, benzoyl, or halo$(C_2-C_6)$alkanoyl; and one, two, or three of J, K, and L are N, provided that when J, K, or L are N, $R_9$, $R_{10}$, and $R_{12}$ are absent at that position comprising:

(a) Oxidation of the alcohol to the aldehyde;
(b) Addition of TMS acetylide to the aldehyde;
(c) Removal of the TMS group by hydrolysis;
(d) Treatment of the acetylene with base and reaction with formaldehyde to form the propargyl alcohol;
(e) Conversion of the primary alcohol to the halide;
(f) Alkylation with "X" to followed byby decarboxylation to form the ester; and
(g) Hydrolysis of the ester to provide the compound of formula IB.

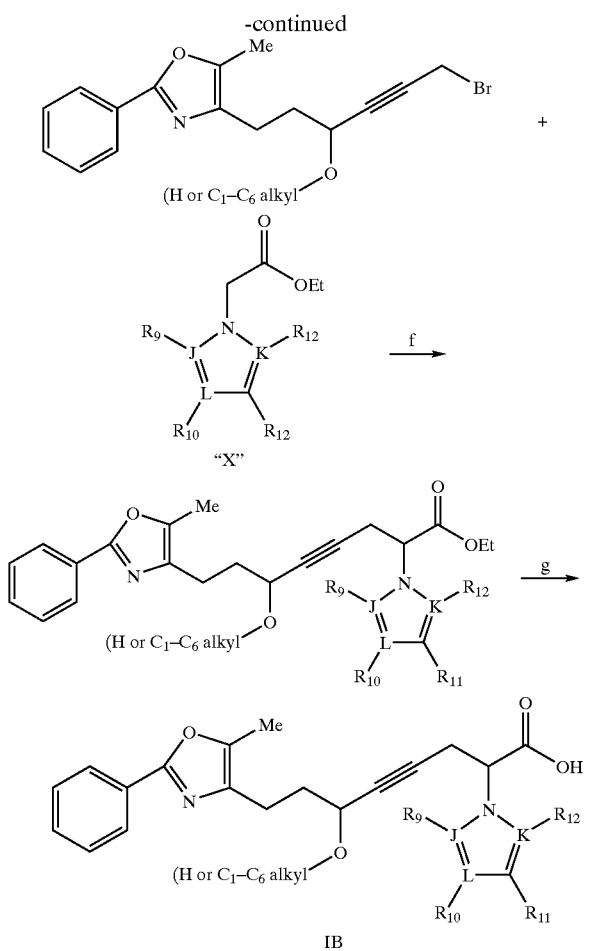

DETAILED DESCRIPTION OF THE INVENTION

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term "alkyl" means a straight or branched hydrocarbon radical having from 1 to 7 carbon atoms and includes, for example, methyl, ethyl, n-propyl, isopropyl, n-butyl, sec-butyl, isobutyl, tert-butyl, n-pentyl, n-hexyl, n-heptyl, n-octyl, 2-isopropylheptyl.

The term "aryl" means a cyclic or polycyclic aromatic ring having from 5 to 12 carbon atoms, and being unsubstituted or substituted with up to 3 of the substituent groups recited above for alkyl, alkenyl, and alkynyl. Examples of aryl groups include phenyl, 2,6-dichlorophenyl, 3-methoxyphenyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl.

The term "heteroaryl" means an aromatic cyclic or fused polycyclic ring system having from 1 to 8 heteroatoms selected from N, O, and S. The heteroaryl groups or fused heteroaryl groups may be unsubstituted or substituted by 1 to 3 substituents selected from those described above for alkyl, alkenyl, and alkynyl, for example, cyanothienyl and formylpyrrolyl.

Typical heteroaryl groups include 2- or 3-thienyl, 2- or 3-furyl, 2- or 3-pyrrolyl, 2-, 4-, or 5-imidazolyl, 3-, 4-, or 5-, pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazoyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

Aromatic fused heteroaryl groups of from 8 to 20 atoms include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-, perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b] furanyl, 2-, 3-, 5-, 6-, 7-, 8-, 9-, 10-, or 11-7H-pyrazino[2, 3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4, 5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8- or 9-furo [3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2, 4]triazinyl, 7-benzo[b]thienyl, 2-4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2] benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

Particuular heteroaryl groups of use in the context of the instant invention which may be substituted or unsubstituted include the following groups wherein "∿∿∿" indicates the point of attachment.

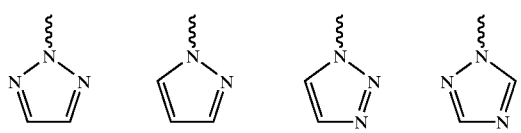

The alkyl, aryl, and heteroaryl can be substituted with 1 to 4 groups selected from halo, hydroxy, cyano, $C_1-C_6$ alkoxy, nitro, nitroso, amino, $C_1-C_6$ alkylamino, di-$C_1-C_6$ alkylamino, carboxy, $C_1-C_6$ $C_1-C_6$ alkanoyl, $C_1-C_6$ alkoxycarbonyl, aminocarbonyl, halomethyl, dihalomethyl, trihalomethyl, haloethyl, dihaloethyl, trihaloethyl, tetrahaloethyl, pentahaloethyl, thiol, $(C_1-C_4)$alkylsulfanyl, $(C_1-C_4)$alkylsulfinyl, and aminosulfonyl. Examples of substituted alkyl groups include fluoromethyl, tribromomethyl, hydroxymethyl, 3-methoxypropyl, 3-carboxypentyl, 3,5-dibromo-6-aminocarbonyidecyl, and 4-ethylsulfinyloctyl.

The term "prodrug" denotes a compound that is converted in vivo to an active compound. The term "prodrug group" denotes a moiety that is converted in vivo into the active compound of formula I wherein E is substituted heteroaryl or —CO$_2$H. Such groups are generally known in the art and include ester forming groups, that form an ester prodrug, such as benzyloxy, di(C$_1$–C$_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and (C$_1$–C$_6$)alkoxy optionally substituted by N-morpholino and amide-forming groups such as di(C$_1$–C$_6$) alkylamino. Other prodrug groups include C$_1$–C$_6$ alkoxy, and O$^-$ M$^+$ where M$^+$ represents a cation. Preferred cations include sodium, potassium, and ammonium. Other cations include magnesium and calcium. Further prodrug groups include O$^=$M$^{++}$, where M$^{++}$ is a divalent cation such as magnesium or calcium.

The term "diabetes" refers to one metabolic disorder in which there is impaired glucose utilization inducing hyperglycemia. An overview of the pathogenesis and morphology of diabetes and its late complications is available to practitioneres of the art, for instance, in Robins' *Pathologic Basis of Disease* (5$^{th}$. Ed., pp. 910–922). Other metabolic disorders associated with impaired glucose utilization and insulin resistance include IRS, described previously. In addition to the major late-stage complications of NIDDM (diabetic angiopathy, atherosclerosis, diabetic nephropathy, diabetic neuropathy, and diabetic ocular complications such as retinopathy, cataract formation and glaucoma), many other conditions are linked to NIDDM, including dyslipidemia glucocortcoid induced insulin resistance, dyslipidemia, polycysitic ovarian syndrome, obesity, hyperglycemia, hyperlipidemia, hypercholerteremia, hypertriglyceridemia, hyperinsulinemia, and hypertension. Brief definitions of these conditions are available in any medical dictionary, for instance, *Stedman's Medical Dictionary* (Xth Ed.).

It will be appreciated by those skilled in the art that compounds of the invention having a chiral center may exist in and be in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity or cytotoxicity using the standard tests described herein, or using other similar tests which are well known in the art.

Specific and preferred values listed below for radicals, substituents, and ranges, are for illustration only; they do not exclude other defined values or other values within defined ranges for the radicals and substituents Specifically, (C$_1$–C$_6$) alkyl can be methyl, ethyl, propyl, isopropyl, butyl, isobutyl, sec-butyl, pentyl, 3-pentyl, or hexyl;.

(C$_1$–C$_6$)alkoxy can be methoxy, ethoxy, propoxy, isopropoxy, butoxy, iso-butoxy, sec-butoxy, pentoxy, 3-pentoxy, or hexyloxy; (C$_1$–C$_6$)alkanoyl can be acetyl, propanoyl or butanoyl.

Halo(C$_1$–C$_6$)alkyl can be iodomethyl, bromomethyl, chloromethyl, fluoromethyl, trichloromethyl, trifluoromethyl, 2-chloroethyl, 2-fluoroethyl, 2,2,2-trifluoroethyl, or pentafluoroethyl.

(C$_1$–C$_6$)alkanoyloxy can be formyloxy, acetoxy, propanoyloxy, butanoyloxy, isobutanoyloxy, pentanoyloxy, or hexanoyloxy.

Aryl can be phenyl, indenyl, or naphthyl.

Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, in a compound of formula I, a value for X is

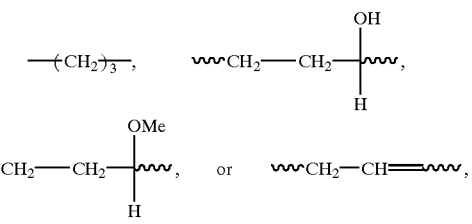

wherein "$\sim\!\sim\!\sim$" indicate points of attachment.

B is H.

E is CO$_2$H.

Y is —CH$_2$—.

R$_9$–R$_{12}$ are each independently H, halo, aryl, (C$_1$–C$_6$) alkyl, halo(C$_1$–C$_6$)alkyl, (C$_1$–C$_6$)alkanoyl, halo (C$_1$–C$_6$)alkanoyl, benzoyl, or halo(C$_2$–C$_6$)alkanoyl.

Also, one, two, or three of J, K, and L can be N, provided that when J, K, or L are N, R$_9$, R$_{10}$, and R$_{12}$ are absent at that position.

In another embodiment of a compound of formula I, X is —CH$_2$CH$_2$CH$_2$—.

B is H.

E is CO$_2$H.

Y is —CH$_2$—.

R$_9$–R$_{12}$ are each independently H, halo, aryl, (C$_1$–C$_6$) alkyl, halo(C$_1$–C$_6$)alkyl, (C$_1$–C$_6$)alkanoyl, halo (C$_1$–C$_6$)alkanoyl, benzoyl, or halo(C$_2$–C$_6$)alkanoyl.

Also, one, two, or three of J, K, and L can be N, provided that when J, K, or L are N, R$_9$, R$_{10}$, and R$_{12}$ are absent at that position.

In another embodiment of a compound of formula I, X is —CH$_2$CH$_2$CH$_2$—.

B is H.

E is CO$_2$H.

Y is —CH$_2$—.

R$_{11}$ is H.

J—R$_9$ is N or CH.

K—R$_{12}$ is N or CH; and

L—R$_{10}$ is CH.

In another embodiment of a compound of formula I, X is —CH$_2$CH$_2$CH$_2$—.

B is H.

E is CO$_2$H.

Y is —CH$_2$—.

R$_{11}$ is H.

J—R$_9$ is N or CH.

K—R$_{12}$ is CH; and

L—R$_{10}$ is N.

In another embodiment of a compound of formula I, X is
—CH$_2$CH$_2$CH$_2$—.
B is H.
E is CO$_2$H.
Y is —CH$_2$—.
R$_{11}$ is H.
J—R$_9$ is CH.
K—R$_{12}$ is N or CH; and
L—R$_{10}$ is N or CH.
In another embodiment of a compound of formula I, X is

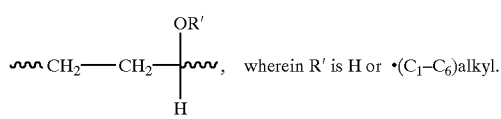

B is H.
E is CO$_2$H.
Y is —CH$_2$—.
R$_9$–R$_{12}$ are each independently H, halo, aryl, (C$_1$–C$_6$) alkyl, halo(C$_1$–C$_6$)alkyl, (C$_1$–C$_6$)alkanoyl, halo (C$_1$–C$_6$)alkanoyl, benzoyl, or halo(C$_2$–C$_6$)alkanoyl.
Also, one, two, or three of J, K, and L are N, provided that when J, K, or L are N, R$_9$, R$_{10}$, and R$_{12}$ are absent at that position.
In another embodiment of a compound of formula I, X is

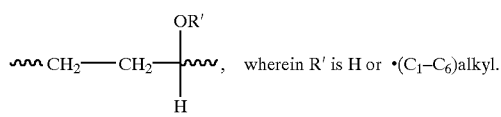

B is H;
E is CO$_2$H.
Y is —CH$_2$—.
R$_{11}$ is H.
J—R$_9$ is N or CH.
K—R$_{12}$ is N or CH; and
L—R$_{10}$ is CH.
In another embodiment of a compound of formula I, X is

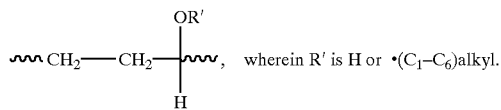

B is H;
E is CO$_2$H.
Y is —CH$_2$—.
R$_{11}$ is H.
J—R$_9$ is CH.
K—R$_{12}$ is N or CH; and
L—R$_{10}$ is N or CH.
In another embodiment of a compound of formula I, X is

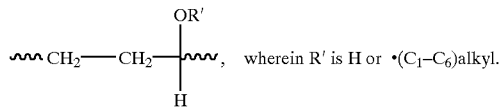

B is H;
E is CO$_2$H.
Y is —CH$_2$—.

R$_{11}$ is H.
J—R$_9$ is N or CH.
K—R$_{12}$ is CH; and
L—R$_{10}$ is N.

Processes and novel intermediates for preparing compounds of formula I are provided as further embodiments of the invention and are illustrated by the following procedures in which the meanings of the generic radicals are as given above unless otherwise qualified.

Scheme 1 depicts one approach to preparing compounds of the invention which are compounds of formula IA. Thus, displacement of the mesylate group in 1-1 with cyanide provides the nitrile 1-2. The nitrile 1-2 is then hydrolyzed to the corresponding carboxylic acid 1-3. The acid 1-3 is reduced to the primary alcohol 1-4 and converted to the halide 1-5 (such as the bromide, although the chloride or iodide can also be made), under Finkelstein-type conditions. The bromide 1-5 is them treated with lithium trimethylsilylacetylide to provided the TMS-protected acetylene 1-6. The TMS group is removed from 1-6, geneneating the free acetylene 1-7. The acetyelene 1-7 is then treated with based and allowed to undergo reaction with formaldehyde to provide the propargyl alcohol 1-8. The primary alcohol 1-8 is then converted to the halide 1-9 using the conditions indicated earlier. The bromide is then used as the alkylating agent in the presence of "X" to prepare the target compound 1-10 as the ester, after decarboxylation of the malonate. The ester 1-10 is then converted to the invention compound IA.

Scheme 1

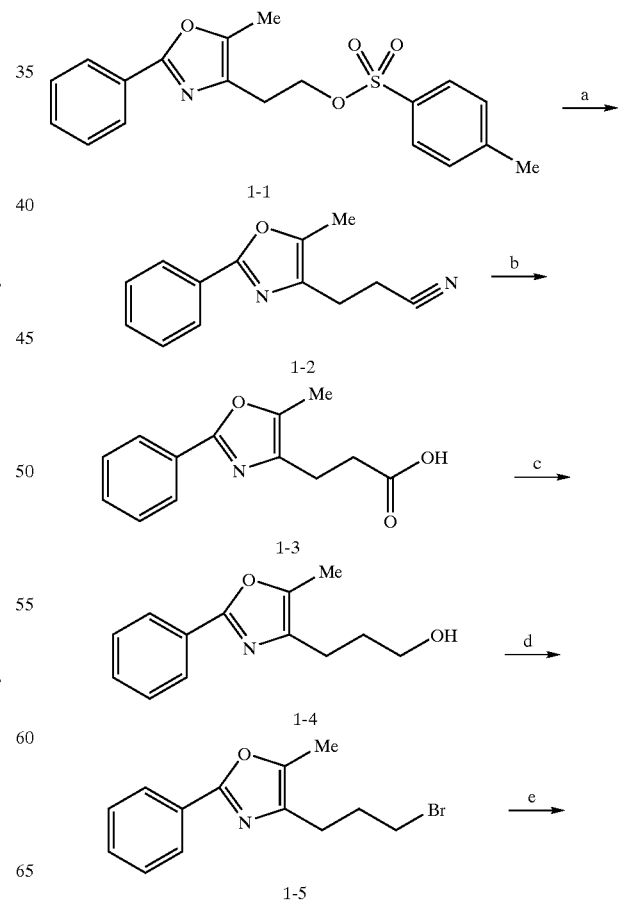

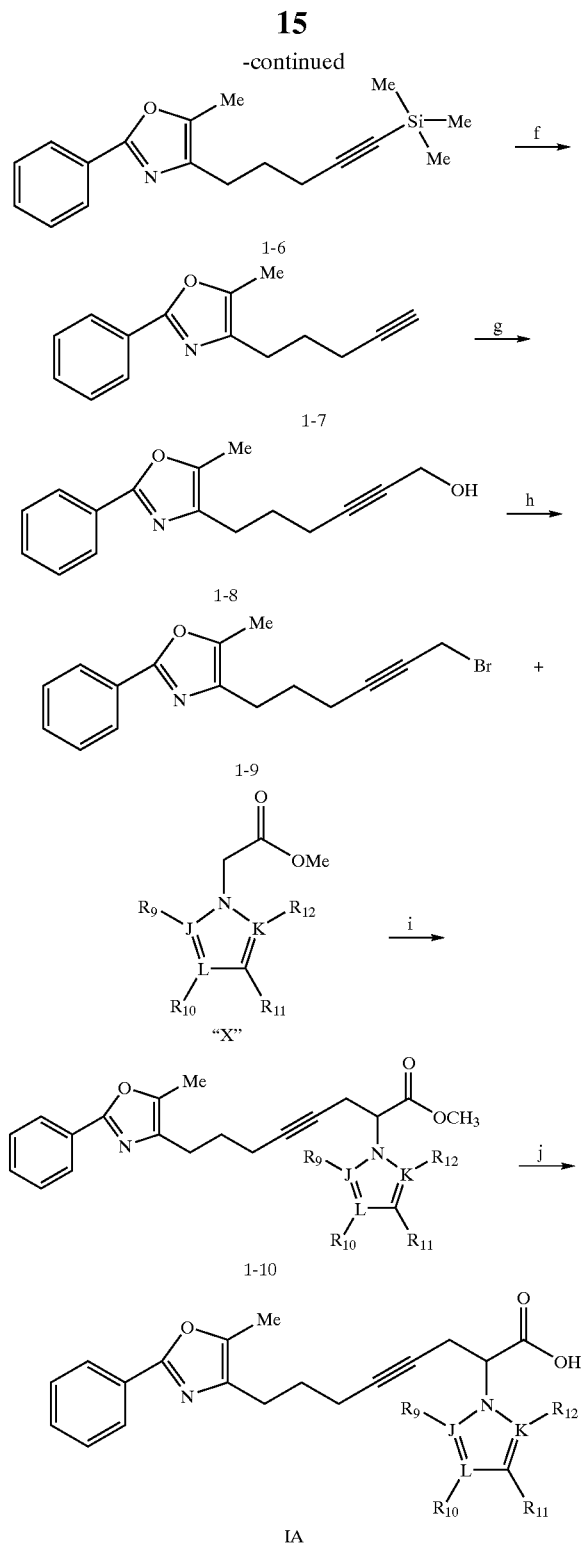

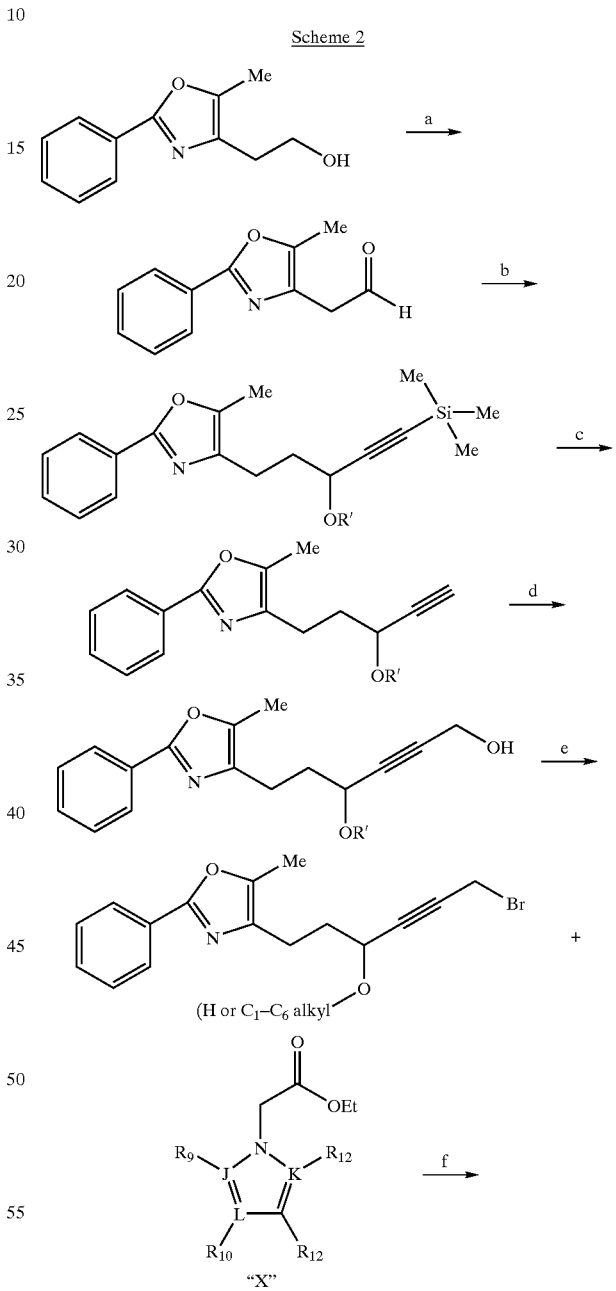

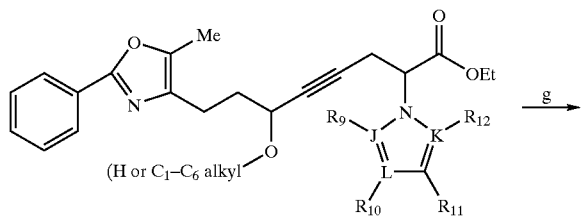

acetylene 2-3 is treated with base, then quenched with formaldehyde to provide the propargyl alcohol 2-4. The primary alcohol 2-4 is then converted to the halide 2-5 using the conditions indicated earlier. The bromide 2-5 is then used as the alkylating agent in the presence of "X" to prepare the target compound 2-6 as the ester, after decarboxylation of the malonate. The ester 2-6 is then converted to the invention compound IA.

An additional approach to invention compounds which are compounds of formula IB is provided in the Scheme 2. Thus, the primary alcohol in 1-1 is oxidized to the corresponding aldehyde 2-1 under conditions available to the skilled artisan. The aldehyde 2-1 is then treated with lithium trimethylsilyl acetylide to provide the secondary alcohol 2-2, which optionally may be protected as an acetate, or converted to the methyl ether. The trimenthylsilyl group in 2-2 is removed to provide the free acetylene 2-3. The

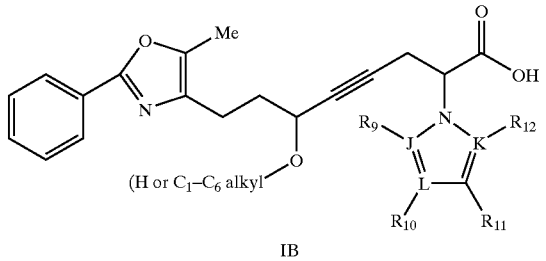

IB

Certain compounds of formula I are useful as intermediates for preparing other compounds of formula I. It is also noted that compounds of formula I can be prepared using protecting groups and protecting group chemistry. The appropriate use and choice of protecting groups is well-known by one skilled in the art, and is not limited to the specific examples below. It is also to be understood that such groups not only serve to protect chemically reactive sites, but also to enhance solubility or otherwise change physical properties. A good general reference for protecting group preparation and deprotection is "Protecting Groups in Organic Synthesis" by T. W. Green and P. G. Wuts. A number of general reactions such as oxidations and reductions etc. are not shown in detail but can be done by methods understood by one skilled in the art. General transformations are well-reviewed in "Comprehensive Organic Transformation" by Richard Larock, and the series "Compendium of Organic Synthetic Methods" published by Wiley-Interscience. In general, the starting materials are obtained from commercial sources unless otherwise indicated.

Some of the compounds of Formula I are capable of further forming pharmaceutically acceptable acid-addition and/or base salts. All of these forms are within the scope of the present invention.

Pharmaceutically acceptable acid addition salts of the compounds of formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogen phosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M. et al., "Pharmaceutical Salts," *Journal of Pharmaceutical Science*, 1977;66:1–19).

The acid addition salt of basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., supra., 1977).

The base addition salts of acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms, as well as the appropriate mixtures thereof.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include orotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.005 to about 100 mg/kg, e.g., from about 0.1 to about 75 mg/kg of body weight per day, such as 0.03 to about 50 mg per kilogram body weight of the recipient per day, preferably in the range of 0.06 to 90 mg/kg/day, most preferably in the range of 0.15 to 60 mg/kg/day.

The compound may conveniently be administered in unit dosage form; for example, containing 0.05 to 1000 mg, conveniently 0.1 to 750 mg, most conveniently, 0.5 to 500 mg of active ingredient per unit dosage form.

Ideally, the active ingredient should be administered to achieve peak plasma concentrations of the active compound of from about 0.005 to about 75 $\mu$M, preferably, about 0.01 to 50 $\mu$M, most preferably, about 0.02 to about 30 $\mu$M. This may be achieved, for example, by the intravenous injection of a 0.0005 to 5% solution of the active ingredient, optionally in saline, or orally administered as a bolus containing about 0.01–1 mg of the active ingredient. Desirable blood levels may be maintained by continuous infusion to provide about 0.0001–5 mg/kg/hr or by intermittent infusions containing about 0.004–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The antidiabetes ability of a compound of the invention is demonstrated using pharmacological models that are well known to the art, for example, using models such as the tests described below.

TEST A—3T3-L1 Adipocyte Differentiation Assay (ADPDIFF)

This assay is used to determine the potential of putative PPAR-$\gamma$ ligands to induce fat cell differentiation. A quantitative method was established for determining the ability of potential PPAR-$\gamma$ ligands to promote adipogenesis of 3T3-L1 preadipocytes. 3T3-L1 preadipocytes are plated onto 96 well plates (20,000 cells per well). Upon confluency, the compounds which were initially scored as positives from the PPAR-$\gamma$ ligand displacement and PPAR-$\gamma$ chimeric receptor transcription assays were added for 4 days with the final concentrations of 2.5, 5.0 and 10 $\mu$M (n=3). Each plate contains positive controls (5 uM BRL 49653 and 5 uM Troglitazone) and a vehicle control (DMSO). Cells are replenished with FBS containing media on day 5 of post-drug treatment and incubated for additional 4–6 days. Cells are stained with BODIPY a fluorescent lipophilic stain to quantitate the lipid content of the cells. The assay is optimized for a 96-well plate format. Approximately after 10 days of post-drug treatment, cells are fixed in 3% formalin solution for 15 min followed by staining with BODIPY (80 µg/ml) for 20 min at room temperature. The plate is then put through the CYTOFLUOR instrument to measure the fluorescence of BODIPY (excitation=485/20; emission=530/25). A template is created in a spread sheet to calculate the average value of BODIPY measurements and reported as % of BRL 49653 at 5 µM.

TEST B—ANTCV1 Antagonist Transcription Assay

The ANTCV1 transcription assay is an in vitro assay in which CV-1 cells, an African green monkey kidney cell line, are transfected with a luciferase reporter construct comprised of a fragment of the fatty acid binding protein (FATP) promoter located upstream of the TK TATA box. Transfection efficiency is controlled by co-transfectionof the reference plasmid CMV β-galactosidase. The DNAs are transiently transfected into the cells by electroporation and the cells are plated into 96-well dishes. Test compounds are diluted to final concentration of 25 µM in individual wells containing 300 nM BRL. Control wells include either the 0.5% DMSO vehicle control, the antagonist PD 0157724-0000 at 25 µM and 300 nM BRL, or 300 nM BRL alone. Cells are incubated with both the drugs for 48 hrs and then harvested. The lysates are measured for luciferase and β-galactosidase activities using the dual luciferase kit from Tropix on a EG&G Berthold MicroLumat LB96P luminometer. The fold activation of BRL 49653 in each assay must be above 4 in order for the assay to be considered valid.

Raw numbers are transferred to an Excel spreadsheet and luciferase/β-galactosidase ratios are determined for each compound. The percent BRL 49653 inhibition for each compound is calculated by dividing the luciferase/β-galactosidase ratio for each compound by the luciferase/β-galactosidase ratio of the DMSO vehicle control. This number is then plugged into the following equation:

% BRL inhibition=(BRL fold activation−test compound fold activation & BRL/BRL fold activation−1)×100.

TEST C—CV-1 NATIVE RECEPTORS TRANSCRIPTION ASSAY (MKNRCV1)

The purpose of this assay is to identify ligands that activate endogenous nuclear receptors in CV-1 cells. Protocol: CV-1 cells are co-transfected with a luciferase reporter containing a fragment of the FATP promoter upstream the TK TATA box and a CMV beta-galactosidase plasmid. Transfected cells are incubated with test ligands for 48 hours. Cell lysates are harvested and the luciferase and beta-galactosidase activities are determined. Description: Luciferase and beta-galactosidase activities in the cell lysates are measured using an EG&G Berthold luminometer. These values are entered into and Excel worksheet which calculates the luciferase to beta-galactosidase ratios and expresses the data as percent activity of the reference compound, BRL 49653.

TEST D—BLOOD GLUCOSE MEASURMENT (GLUCOSE Δ)

Glucose is obtained 4 hours post dose via tail vein stick (5 µl whole blood) in awake, 4 hour fasted animals. Blood is drawn by capillary action into a glucose cuvette and read in a HemoCue Glucose Analyzer (Ryan Diagnostics). Blood is diluted 1:2 with saline if glucose levels are greater than 400 mg/dl (meter high range) and results multiplied by two.

TEST E—3T3-L1 TRANSIENT REPORTER ASSAY

This assay is used to determine the potential of putative PPAR-γ ligands to activate the promoter/enhancer of the murine aP2 gene. 3T3-L1 preadipocytes are cultured on collagen coated plates in DMEM containing 10% Calf serum for 48 hours post-confluence. The cells are then cultured for approximately 3 days in DMEM containing 10% Fetal Bovine Serum (FBS), 0.5-mM methyl isobutylxanthine, 0.25 µM dexamethasone, and 1 µg/ml of insulin. Cells are detached from the plates with Trypsin-EDTA and resuspended in Phosphate Buffered Saline (PBS).

The reporter construct used in this assay is comprised of the —5.4 Kb 5' flanking region of the murine aP2 gene inserted into the cloning site of the TKpGL3 luciferase vector. Transfection efficiency is controlled by co-transfection of the reference plasmid CMV-β-galactosidase. The reporter construct and the reference plasmid are transiently co-transfected into the cells by electroporation. The transfected cells are plated into collagen coated 96-well plates and cultured overnight. Cells are then incubated for 48 hours with the test compounds and then harvested. The lysates are measured for luciferase and β-galactosidase activities using the Dual-Light® luciferase kit from Tropix on a EG&G Berthold MicroLumat LB96P luminometer.

Data are summarized in Table 1.

TABLE 1

| | Biological Activity of PD 338228 and analogs | | | | |
| --- | --- | --- | --- | --- | --- |
| | | | AD3T3-L1 Reporter | | In VIVO |
| Example | Structure | EC$_{50}$(nM) | Max. % Rosi | Δ Glucose @ 20 mg/kg | % Rosiglitazone |
| 1-13 | 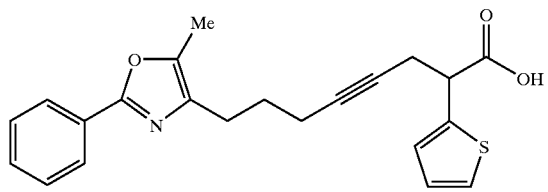 | 303 | 97 | Not tested | |

TABLE 1-continued

Biological Activity of PD 338228 and analogs

| Example | Structure | AD3T3-L1 Reporter EC$_{50}$(nM) | Max. % Rosi | In VIVO Δ Glucose @ 20 mg/kg | % Rosiglitazone |
|---|---|---|---|---|---|
| 1-11 | (structure) | 89 | 108 | Not tested | |
| 1-15 | (structure) | 15 | 103 | −258 mg/dL | 180% |

In general, compounds of the invention may induce fat cell differentiation as described in test A. Results from test B, in particular, demonstrate that the compounds of the invention may lower glucose levels in mice.

Compounds of the invention induce adipocyte differentiation and lower blood glucose levels. As such, they may be useful in treating disorders associated with insulin resistance. Such disorders include: NIDDM, diabetic angiopathy, atherosclerosis, diabetic nephropathy, diabetic neuropathy, and diabetic ocular complications such as retinopathy, cataract formation and glaucoma, as well as glucocortcoid induced insulin resistance, dyslipidemia, polycysitic ovarian syndrome, obesity, hyperglycemia, hyperlipidemia, hypercholerteremia, hypertriglyceridemia, hyperinsulinemia, and hypertension.

Accordingly, the invention also includes a method for treating a disease in a human or other mammal in need thereof in which insulin resistance has been implicated and glucose lowering is desired, comprising administering to said human or mammal an effective amount of a compound of formula I or a pharmaceutically acceptable salt thereof. The invention also includes a method for treating or preventing insulin resistance in a mammal comprising administering to said mammal an effective amount of a compound of formula I or a pharmaceutically acceptable salt thereof. Additionally, compounds of the invention can be used in vitro or in vivo as pharmacological and biochemical tools to assist in the discovery and evaluation of other glucose lowering agents and PPAR γ agonists.

Esters of the general formula 1-10 or 2-6 (see Schemes 1 and 2) are readily hydrolyzed to compounds of the invention. Accordingly, the invention also includes a method of preparing a compound of formula I by hydrolyzing a compound of formula 1-10 or 2-6

Additionally, esters of the general formula 1-10 or 2-6 may be determined to function as prodrugs for compounds of formula I. Accordingly, the invention also includes a method for treating a disease in a human or other mammal in need thereof in which insulin resistance has been implicated and glucose lowering is desired, comprising administering to said human or mammal an effective amount of a compound of formula 1-10 or 2-6; or a pharmaceutically acceptable salt thereof.

The following non-limiting examples and related biological data are meant to further demonstrate the invention.

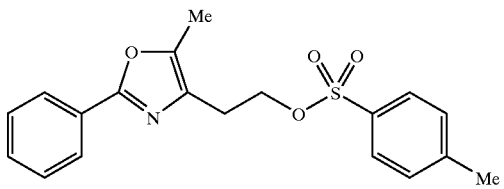

Synthesis of Toluene-4-sulfonic Acid 2-(5-Methyl-2-phenyl-oxazol-4-yl)-ethyl Ester (1-1).

To a solution of 2-(5-Methyl-2-phenyl-oxazol-4-yl)-ethanol (12.5 g, 61 mmol) in dichloromethane (200 mL) at −20° C. under N$_2$ atmophere was added triethylamine (26 mL, 184 mmol) and catalytic amount of 4-dimethylamino pyridine (50 mg). This solution was then treated with toluenesulfonyl chloride (14.1 g, 73.8 mmol) and the reaction was allowed to equilibrate to 23° C. over 16 hours. Reaction was washed with water, 5% Na$_2$CO$_3$, saturated NH$_4$Cl, and brine. Solvent was removed in vacuo and crude tosylate 1 (21.3 g) was carried on to the next step without further purification. M+1=358.2

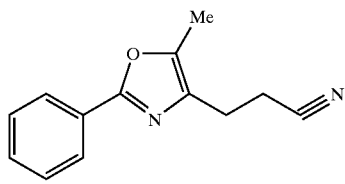

Synthesis of 3-(5-Methyl-2-phenyl-oxazol-4-yl)-propionitrile (1-2).

Methanesulfonate 1-1 (21 g, 59 mmol) was added to a suspension of KCN (7.8 g, 120 mmol) in DMSO (100 mL) and stirred at 23° C. for 16 hours then heated to 50° C. for 2 hours. The reaction was further diluted with water and extracted with dichloromethane (3×200mL). Organic layers were combined, dried over $MgSO_4$, and removed in vacuo to give 12.4 g of crude nitrile 1-2 which was carried on to the next step without further purification. M+1=213.1

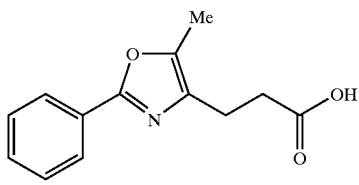

Synthesis of 3-(5-Methyl-2-phenyl-oxazol-4-yl)-propionic Acid (1-3).

KOH (13g, 235 mmol) was added to a mixture of ethanol/water (100 mL/100 mL) containing nitrile 1-2 (12.4 g, 58.68 mmol) and refluxed for 8 hours. Ethanol was removed in vacuo and the residue was acidified to pH=2 with aqueous HCl. The precipitated solid was filtered, washed with water, and dried in a vacuum oven overnight. The recoverd 13.5 g of acid 1-3 was used in the following step with no further purification. NMR $CDCl_3$ ($\delta$): 7.97 (2H, m); 7.45 (3H, m); 2.84 (4H, m); 2.35 (3H, s). M+1=232.1

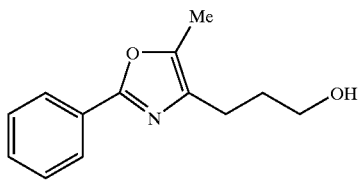

Synthesis of 3-(5-Methyl-2-phenyl-oxazol-4-yl)-propan-1-ol (1-4).

Acid 1-3 (4.6 g, 20 mmol) was dissolved in 300 mL of a 1:1 mixture of methanol/toluene at 23° C. under $N_2$ atmosphere. Trimethylsilyl diazomethane (20 mL, 40 mmol), added dropwise until color persisted and stirred for an additional 4 hours. Solvent was removed in vacuo and residue dried under vacuum for 1 hour. Residue was then redissolved in 300 mL methanol and placed under $N_2$ atmosphere. $NaBH_4$ (10 g, 264 mmol)and the reaction stirred for 4 hours. When complete, solvent was removed in vacuo and residue taken up in ethyl acetate and washed with water, brine and dried over $MgSO_4$. $SiO_2$ chromatography with 40% EtOAc/Hexanes gave 3.1 g of the product 1-4 as white crystals (71%) M.P. NMR $CDCl_3$ ($\delta$): 8.01 (2H, m); 7.44 (3H, m); 3.75 (2H, t, J=5.8, 11.4 Hz); 2.68 (2H, t, 6.8, 13.7 Hz); 2.35 (3H, s); 1.91 (2H, m).

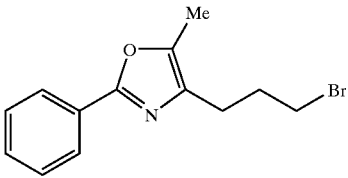

Synthesis of 4-(3-Bromo-propyl)-5-methyl-2-phenyl-oxazole (1-5).

Alcohol 1-4 (3 g, 13.8 mmol) was dissolved in dichloromethane (200 mL) and cooled to 0° C. under $N_2$ atmosphere. Triphenylphosphine (4.35 g, 16.6 mmol) was added followed by $CBr_4$ (5.5 g, 16.6 mol) in small portions. Reaction temperature was allowed to equilibrate to 23° C. over 8 hours. 20 g of $SiO_2$ gel was added and solvent removed in vacuo. The dried silica gel was placed in a filter and washed with 10% EtOAc/Hexanes. The filtrate was reduced to minimum volume and chromatographed with 5–10% EtOAc/Hexanes to give 3.5 g of the product 1-5 as a clear oil (90% yield). M+1=280.0/282.1.

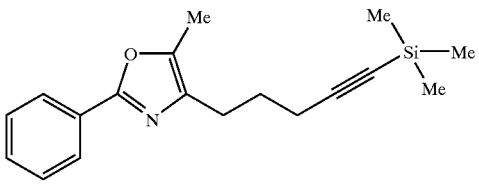

Synthesis of 5-Methyl-2-phenyl-4-(5-trimethylsilanyl-pent-4-ynyl)-oxazole (1-6).

Bromide 1-5 (3.2 g, 12.2 mmol) was dissolved in a 1:1 mixture of THF:DMPU (200 mL) and cooled to 0° C. under $N_2$ atmosphere. Trimethylsilyl lithium acetylide (50mL, 25 mmol) was added to the solution via syringe and allowed to equilibrate to 23° C. for 16 hours. The solution was partitioned between water and EtOAc in a separatory funnel. Organic layer was washed with water, brine, and dried over $MgSO_4$. Solvent removed in vacuo and residue chromatographed with 5% EtOAc/hexanes to give 1.9 g of the product as a clear oil (50% yield). NMR $CDCl_3$ ($\delta$): 7.82 (2H, m); 7.27 (3H, m);2.46 (2H, m); 2.20 (3H, s); 2.10 (2H, m); 1.76 (2H, m); 0.01 (9H, s). M+1=298.1

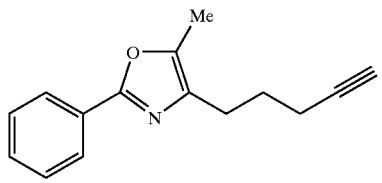

Synthesis of 5-Methyl-4-pent-4-ynyl-2-phenyl-oxazole (1-7)

Alkyne 1-6 (1.9 g, 6.3 mmol) was dissolved in methanol (100 mL) at 23° C. under $N_2$ atmosphere. An aqueous solution of 10% KOH (10 mL) was then added and the reaction stirred for 12 hours. Solvent removed in vacuo and residue partitioned between ethyl acetate (200 mL) and water (200 mL). The organic layer was washed with water, brine and dried over MgSO$_4$. The crude product 1-7 was used in the following step without further purification.

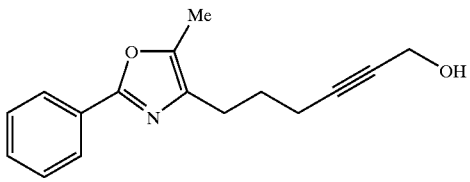

Synthesis of 6-(5-Methyl-2-phenyl-oxazol-4-yl)-hex-2-yn-1-ol (1-8).

Alkyne 1-7 (1.44 g, 6.4 mmol) was dissolved in THF (100 mL) at −78° C. under N$_2$ atmosphere. nBuLi (5.6 mL, 9.0 mmol) was then added and the reaction stirred at −78° C. for 1 hour. Paraformaldehyde (320 mg, 9.6 mmol) was then added in one portion and the reaction stirred while allowing equilibration to 23° C. over 16 hours. Reaction was washed with dilute aqueous HCl, water, brine, and dried over MgSO$_4$. After removing solvent in vacuo chromatography of the residue with 25% EtOAc/Hexanes gave 1.5 g of the product 1-8 as a clear yellowish oil (92%). NMR CDCl$_3$ (δ): 7.97 (@H, m); 7.43 (3H, m); 4.25 (2H, t, J=2.2, 4.4 Hz); 2.60 (2H, t, J=7.3, 14.6 Hz); 2.33 (3H, s); 2.27 (2H, m); 1.89 (2H, m). M+1=256.2.

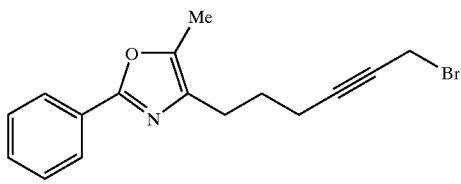

Synthesis of 4-(6-Bromo-hex-4-ynyl)-5-methyl-2-phenyl-oxazole (1-9).

Alcohol 1-8 (1.2 g, 4.7 mmol) was treated in a manner similar to the preparation of bromide 1-5. Chromatography with 10% EtOAc/Hexanes gave the product 1-9 as a colorless oil (1.7 g) in 80% yield. NMR CDCl$_3$ (δ): 7.97 (2H, m); 7.40 (3H, m); 3.93 (2H, s); 2.60 (2H, m); 2.34 (3H, s); 2.28 (2H, m); 1.89 (2H, m).

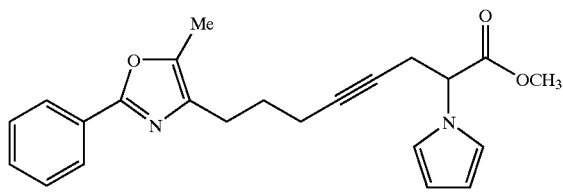

Synthesis of 8-(5-Methyl-2-phenyl-oxazol-4-yl)-2-pyrrol-1-yl-oct-4-ynoic Acid Methyl Ester (1-10).

To a solution of Methyl 2-pyrrolo-acetate (182 mg, 1.31 mmol) in THF/DMF (10 mL/10 mL) at −78° C. under N$_2$ atmosphere was added LiHMDS (1.65 mL, 1.57 mmol) and stirred for 45 min at −78° C. A solution of bromide 9 (500 mg, 1.57 mmol) in THF (10 mL) was added via syringe and the solution was allowed to equilibrate to 23° C. over 0.5 hours. Solution poured into water and extracted with EtOAc. The organic layer was washed with water, brine, and dried over MgSO$_4$. Chromatography with 5% EtOAc gave 190 mg of the product 1-10 as a yellowish oil (38%). NMR CDCl$_3$ (δ): 7.97 (2H, dd, J=1.9, 8.0 Hz); 7.43 (3H, m); 6.78 (2H, t, J=2.2, 4.4 Hz); 6.16 (2H, t, J=2.2, 4.4 Hz); 4.74 (1H, dt, J=7.3, 14.6 Hz); 3.74 (3H, s); 2.92 (2H, M); 2.51 (2H, t, J=7.1, 14.4 Hz); 2.30 (3H, s); 2.15 (2H, q, J=4.4, 6.8, 9.2, 13.6 Hz) M+1=377.

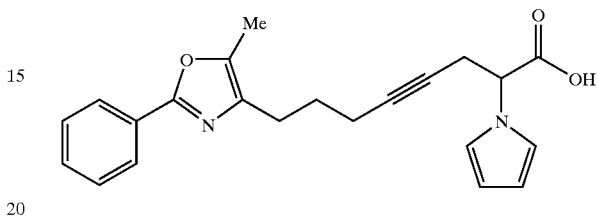

Synthesis of 8-(5-Methyl-2-phenyl-oxazol-4-yl)-2-(propenyl-vinyl-amino)-oct-4-ynoic Acid (1-11)

Ester 1-10 (150 mg, 0.4 mmol) was dissolved in a 1:1 mixture of the product 1-11 as a THF:water at 23° C. LiOH.H$_2$O (20 mg, 0.48 mmol) was added and the solution stirred for 1 hour. Solvent was removed in vacuo and the residue partitioned between EtOAc and aqeous HCl. The organic layer was washed with water, brine, and dried over MgSO$_4$. Removal of solvent in vacuo gave 140 mg of yellowish oil (98%). NMR CDCl$_3$ (δ): 7.92 (2H, m); 7.42 (3H, m); 6.96 (2H, t, J=1.9, 3.6 Hz); 6.19 (2H, t, J=2.2, 3.6 Hz); 4.90 (1H, dd, J=6.3, 8.0 Hz); 2.96 (2H, m); 2.84 (2H, m); 2.33 (3H, s); 2.23 (2H, m); 1.81 (2H, m). M+1=363. CHN (Theor) C=72.91%, H=6.12%, N=13.24%; Obs. 72.11%, H=5.6%, N=7.42%. Biological Data: EC$_{50}$=89 nM in AD3T3-L1 reporter assay. Maximal response of 108% rosiglitazone

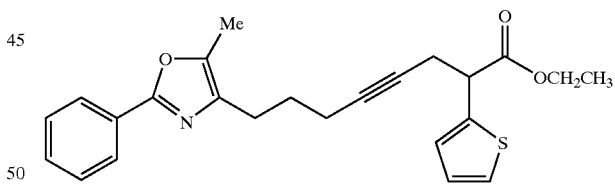

Synthesis of 8-(5-Methyl-2-phenyl-oxazol-4-yl)-2-thiophen-2-yl-oct-4-ynoic Acid Ethyl Ester (1-12)

Prepared in a manner similar to ester 1-10 with the exception that Ethyl 2-thiophene acetate was used instead of Methyl 2-pyrrolo-acetate. Chromatography gave 206 mg of the ethyl ester 1-12 (38% yield) as a yellow oil. NMR CDCl$_3$ (δ): 7.99 (2H, m); 7.43 (3H, m); 7.21 (1H, dd, J=1.0, 5.1 Hz); 6.98 (1H, m); 6.94 (1H, m); 4.22 (2H, m); 4.03 (1H, t, J=7.0, 8.0 Hz), 2.92 (1H, m); 2.71 (1H, m); 2.54 (2H, t, J=7.3, 7.3 Hz); 2.31 (3H, s); 2.14 (2H, m); 1.81 (2H, m); 1.25 (3H, t, J=7.1, 7.1 Hz). M+1=408.2.

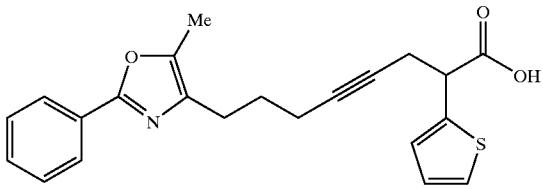

Synthesis of 8-(5-Methyl-2-phenyl-oxazol-4-yl)-2-thiophen-2-yl-oct-4-ynoic Acid (1-13)

The ester 1-12 was then hydrolyzed in a manner similar to the preparation of 1-11 with LiOH.H$_2$O to provide 90 mg of acid 1-13 (47% yield). NMR CDCl$_3$ (δ): 7.97 (2H, m); 7.43 (3H, m); 7.21 (1H, d, J=5.1 Hz); 7.06 (1H, d, J=3.1 Hz); 6.96 (1H, m); 4.21 (1H, dd, J=5.3, 10.7 Hz); 2.89 (2H, m); 2.62 (2H, m); 2.34 (3H, s); 2.23 (2H, m); 1.82 (2H, m). M+1=363.2. Biological Data: EC$_{50}$=303 nM in AD3T3-L1 reporter assay. Maximal response of 97% rosiglitazone.

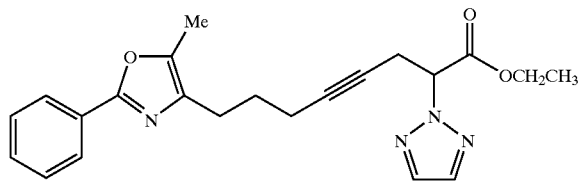

Synthesis of 8-(5-Methyl-2-phenyl-oxazol-4-yl)-2-[1,2,3]triazol-2-yl-oct-4-ynoic Acid Ethyl Ester (1-14)

Potassium t-butoxide (2.6 mL, 2.6 mmol) was added to a to a solution of [1,2,3]triazol-2-yl-acetic acid ethyl ester (355 mg, 2.3 mmol) in THF (30 mL) at −78° C. under N$_2$ atmosphere and stirred for 1 hour. A solution of bromide 1-9 (1.5 g, 4.5 mmol) in THF (30 mL) was then added and the solution allowed to equilibrate to 0° C. for 1 hour. Reaction was then poured into dilute aqueous HCl and diluted with EtOAc. The organic layer was washed with water, brine, and dried over MgSO$_4$. Chromatography with 20% EtOAc/Hex gave 550 mg of a mixture of mono-1-4 and bis-alkylated products. The mixture was not separated, and was taken on to hydrolysis step.

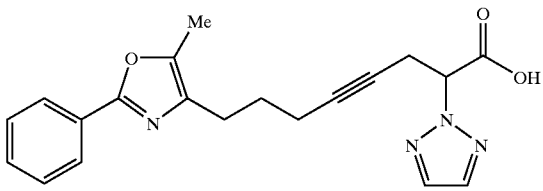

Synthesis of 8-(5-Methyl-2-phenyl-oxazol-4-yl)-2-[1,2,3]triazol-2-yl-oct-4-ynoic Acid (1-15)

The crude ethyl ester 1-14 was then hydrolyzed in a manner similar to the preparation of 1-14 with LiOH.H$_2$O to provide 350 mg of a mixture of acid PD342716 and di-alkylated product. Chromatography with 20% EtOac/Hexanes 1% Acetic acid) gave 130 mg the of desired acid 1-15 as a white powder (15% overall yield for both steps). NMR CDCl$_3$ (δ): 7.92 (2H, m); 7.70 (2H, m); 7.42 (3H, m); 5.53 (1H, m); 3.43 (1H, dd, J=4.8, 16.5 Hz), 3.16 (1H, dd, 2.9, 14.6 Hz); 2.73 (1H, m); 2.63 (1H, m); 2.31 (3H, s); 2.24 (2H, m); 1.76 (2H, m). M+1=365.2 Biological Data: EC$_{50}$= 15 nM in AD3T3-L1 reporter assay. Maximal response of 103% rosiglitazone Normalized blood glucose in Ob/Ob diabetic mouse model in 3 days at 20 mg/Kg

FORMULATION EXAMPLES

The following illustrates representative pharmaceutical dosage forms, containing a compound of Formula I, for therapeutic or prophylactic use in humans.

| (i) | Tablet | mg/tablet |
|---|---|---|
| | Invention Compound | 25.0 |
| | Lactose | 50.0 |
| | Corn Starch (for mix) | 10.0 |
| | Corn Starch (paste) | 10.0 |
| | Magnesium Stearate (1%) | 3.0 |
| | | 300.0 |

The biphenylsulfonamide, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment.

| (ii) | Tablet | mg/capsule |
|---|---|---|
| | Invention Compound | 10.0 |
| | Collodial Silicon Dioxide | 1.5 |
| | Lactose | 465.5 |
| | Pregelatinized Starch | 120.0 |
| | Magnesium Stearate (1%) | 3.0 |
| | | 600.0 |

| (iii) | Preparation for Oral Solution | Amount |
|---|---|---|
| | Invention Compound | 400 mg |
| | Sorbitol Solution (70% N.F.) | 40 mL |
| | Sodium Benzoate | 20 mg |
| | Saccharin | 5 mg |
| | Cherry Flavor | 20 mg |
| | Distilled Water q.s. | 100 mL |

The sorbitol solution is added to 40 mL of distilled water, and the biphenylsulfonamide is dissolved therein. The saccharin, sodium benzoate, flavor, and dye are added and dissolved. The volume is adjusted to 100 mL with distilled water. Each milliliter of syrup contains 4 mg of invention compound.

(iv) Parenteral Solution

In a solution of 700 mL of propylene glycol and 200 mL of water for injection is suspended 20 g of the invention compound. After suspension is complete, the pH is adjusted to 6.5 with 1 N hydrochloric acid, and the volume is made up to 1000 mL with water for injection. The Formulation is sterilized, filled into 5.0 mL ampoules each containing 2.0 mL, and sealed under nitrogen.

| (v) Injection 1 (1 mg/mL) | Amount |
|---|---|
| Invention Compound | 1.0 |
| Dibasic Sodium Phosphate | 12.0 |
| Monobasic Sodium Phosphate | 0.7 |
| Sodium Chloride | 4.5 |
| N Sodium hydroxide solution (pH adjustment to 7.0–7.5) | q.s. |
| Water for injection | q.s. ad 1 mL |

| (vi) Injection 2 (10 mg/mL) | Amount |
|---|---|
| Invention Compound | 10.0 |
| Dibasic Sodium Phosphate | 1.1 |
| Monobasic Sodium Phosphate | 0.3 |
| Polyethylene glyco 400 | 200.0 |
| N hydrochloric acid solution (pH adjustment to 7.0–7.5) | q.s. |
| Water for injection | q.s. ad 1 mL |

| (vii) Injection 2 (10 mg/mL) | Amount |
|---|---|
| Invention Compound | 20.0 |
| Oleic Acid | 10.0 |
| Trichloromonofluoromethane | 5,000.0 |
| Dichlorodifluoromethane | 10,000.0 |
| Dichlorotetrafluoroethane | 5,000.0 |

All patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

(h) Oxidation of the alcohol to the aldehyde;
(i) Addition of TMS acetylide to the aldehyde;
(j) Removal of the TMS group by hydrolysis;
(k) Treatment of the acetylene with base and reaction with formaldehyde to form the propargyl alcohol;
(l) Conversion of the primary alcohol to the halide;
(m) Alkylation with "X" followed byby decarboxylation to form the ester; and (n) Hydrolysis of the ester to provide the compound of formula IB:
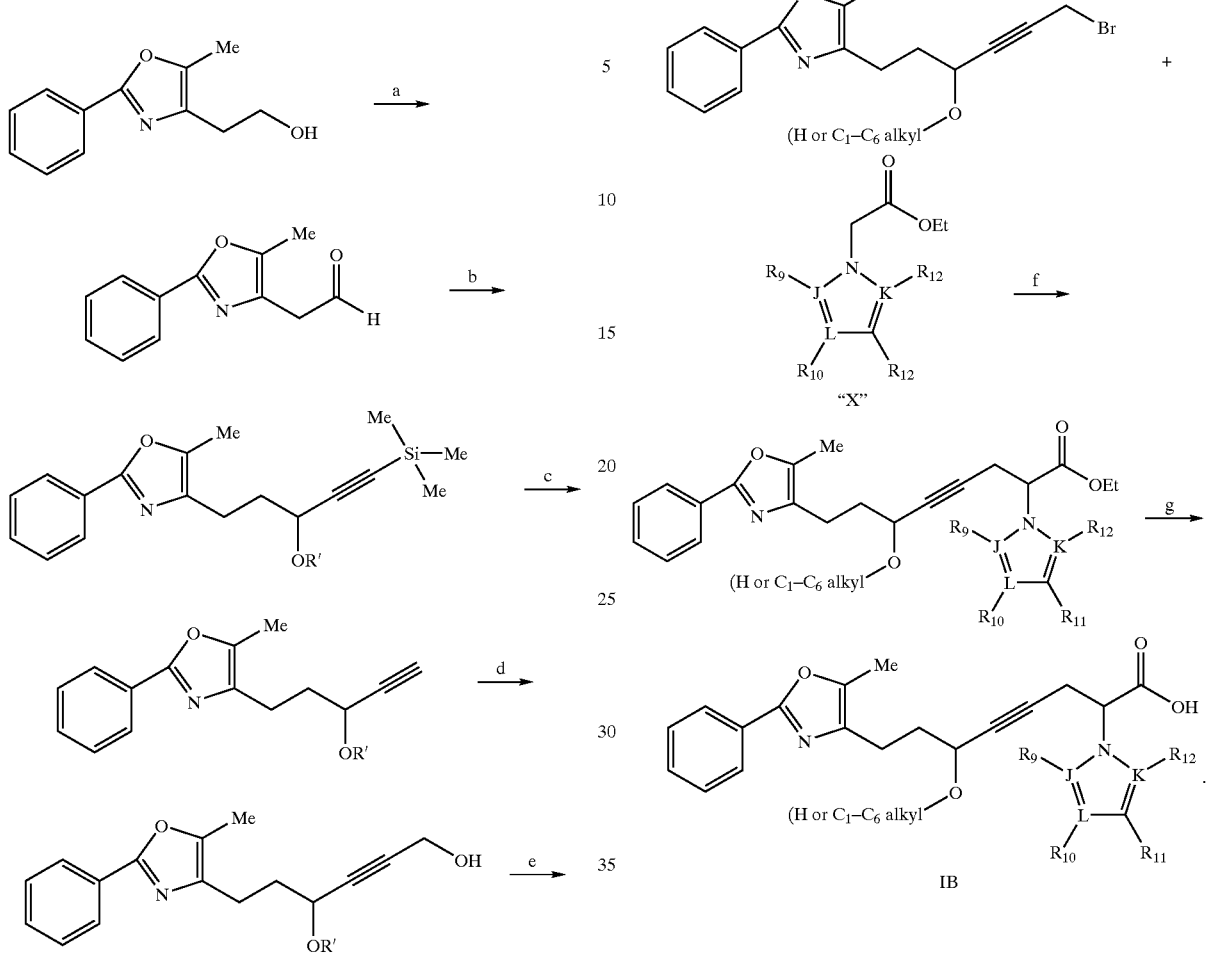

What is claimed is:

1. A compound according to formula (I)

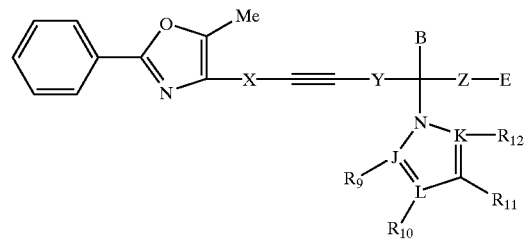

or a pharmaceutically acceptable salt thereof, wherein:

X is $(CR_1R_2)_x$ wherein x is 1, 2, or 3, or X is
—$(CR_3R_4)$—CH=CH—,
—CH=CH—$(CR_3R_4)$—,
—$(CR_3R_4)$—C≡C—,
—C≡C—$(CR_3R_4)$—, wherein $R_1$–$R_4$ are each independently H, OH or $(C_1$–$C_6)$ alkoxy, or $R_3$ and $R_4$ taken together are =O, or $R_3$–$R_6$ are each independently or $(C_1$–$C_6)$alkyl;

Y and Z are $(CR_1R_2)_n$ and $(CR_3R_4)_m$ wherein m and n are each independently 0, 1, 2, or 3;

B is H or $(C_1$–$C_6)$alkyl;

E is $COR_5$, wherein $R_5$ is $(C_1$–$C_6)$alkyl, OH, $(C_1$–$C_6)$ alkoxy, $NR_6R_7$, wherein $R_6$ and $R_7$ are each independently H or $(C_1$–$C_6)$alkyl, or one of $R_6$ and $R_7$ is H or $(C_1$–$C_6)$alkyl and the other is $SO_2R_8$, wherein $R_8$ is H or $(C_1$–$C_6)$alkyl, or E is substituted heteroaryl or

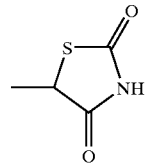

$R_9$–$R_{12}$ are each independently H, halo, aryl, $(C_1$–$C_6)$ alkyl, halo$(C_1$–$C_6)$alkyl, $(C_1$–$C_6)$alkanoyl, halo $(C_1$–$C_6)$alkanoyl, benzoyl, or halo$(C_2$–$C_6)$alkanoyl; and one, two, or three of J, K, and L are N, provided that when J, K, or L are N, $R_9$, $R_{10}$, and $R_{13}$ are absent at that position.

2. The compound of claim 1, wherein

X is —$CH_2CH_2CH_2$—,

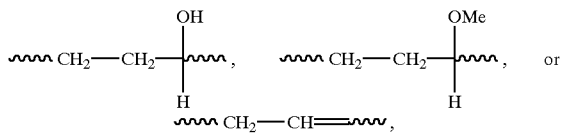

wherein " $\sim\sim\sim$ " indicate points of attachment.

B is H;

E is $CO_2H$; and

Y is —$CH_2$—; and $R_9$–$R_{12}$ are each independently H, halo, aryl, $(C_1$–$C_6)$ alkyl, halo$(C_1$–$C_6)$alkyl, $(C_1$–$C_6)$alkanoyl, halo $(C_1$–$C_6)$alkanoyl, $(C_3$–$C_7)$cycloalkylcarbonyl, benzoyl, or halo$(C_2$–$C_6)$alkanoyl; and one, two, or three of J, K, and L are N, provided that when J, K, or L are N, $R_9$, $R_{10}$, and $R_{12}$ are absent at that position.

3. The compound of claim 2, wherein

X is —$CH_2CH_2CH_2$—;

B is H;

E is $CO_2H$; and

Y is —$CH_2$—; and $R_9$–$R_{12}$ are each independently H, halo, aryl, $(C_1$–$C_6)$ alkyl, halo$(C_1$–$C_6)$alkyl, $(C_1$–$C_6)$alkanoyl, halo $(C_1$–$C_6)$alkanoyl, $(C_3$–$C_7)$cycloalkylcarbonyl, benzoyl, or halo$(C_2$–$C_6)$alkanoyl; and one, two, or three of J, K, and L are N, provided that when J, K, or L are N, $R_9$, $R_{110}$, and $R_{12}$ are absent at that position.

4. The compound of claim 3, wherein $R_{11}$ is H;

J—$R_9$ is N or CH;

K—$R_{12}$ is N or CH; and

L—$R_{10}$ is CH.

5. The compound of claim 3, wherein $R_{11}$ is H;

J—$R_9$ is N or CH;

K—$R_{12}$ is CH; and
L—$R_{10}$ is N.

6. The compound of claim 3, wherein
$R_{11}$ is H;
J—$R_9$ is CH;
K—$R_{12}$ is N or CH; and
L—$R_{10}$ is N or CH.

7. The compound of claim 2, wherein

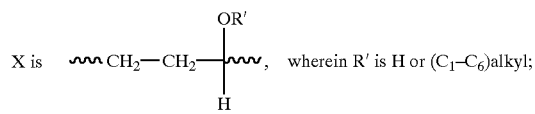

B is H;
E is $CO_2H$;
Y is —$CH_2$—;
$R_{11}$ is H;
J—$R_9$ is N or CH;
K—$R_{12}$ is N or CH; and
L—$R_{10}$ is CH.

8. The compound of claim 2, wherein

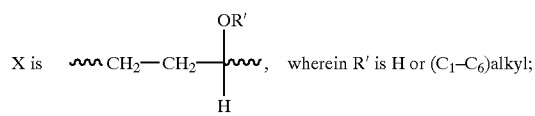

B is H;
E is $CO_2H$;
Y is —$CH_2$—;
$R_{11}$ is H;
J—$R_9$ is N or CH;
K—$R_{12}$ is CH; and
L—$R_{10}$ is N.

9. The compound of claim 2, wherein

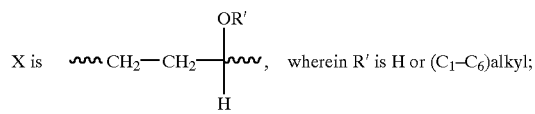

B is H;
E is $CO_2H$;
Y is —$CH_2$—;
$R_{11}$ is H;
J—$R_9$ is CH;
K—$R_{12}$ is N or CH; and
L—$R_{10}$ is N or CH.

10. A compound which is:

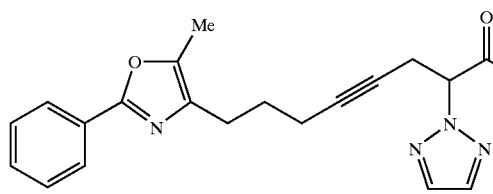

8-(5-Methyl-2-phenyl-oxazol-4-yl)-2-[1,2,3]triazol-2-yl-oct-4-ynoic acid methyl ester;

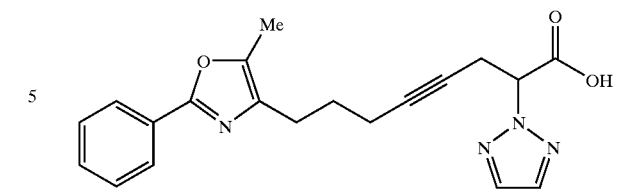

8-(5-Methyl-2-phenyl-oxazol-4-yl)-2-[1,2,3]triazol-2-yl-oct-4-ynoic acid;

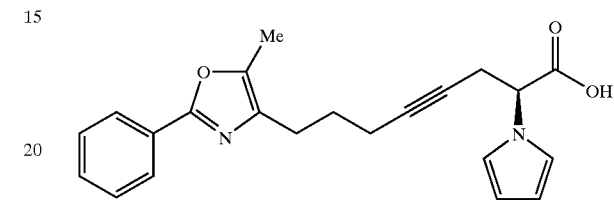

8-(5-Methyl-2-phenyl-oxazol-4-yl)-2-pyrrol-1-yl-oct-4-ynoic acid;

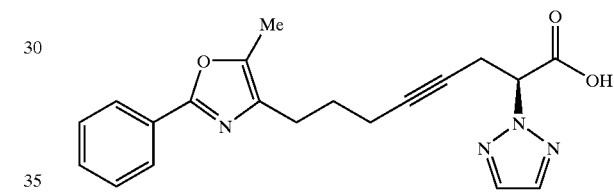

8-(5-Methyl-2-phenyl-oxazol-4-yl)-2-[1,2,3]triazol-2-yl-oct-4-ynoic acid;

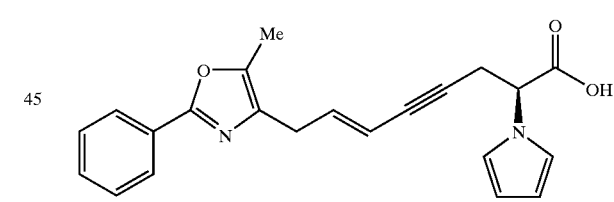

8-(5-Methyl-2-phenyl-oxazol-4-yl)-2-pyrrol-1-yl-oct-6-en-4-ynoic acid;

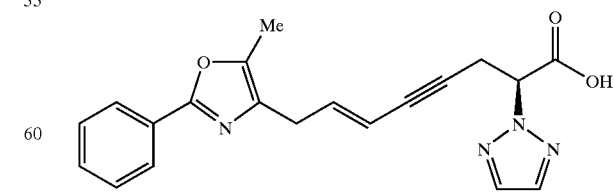

8-(5-Methyl-2-phenyl-oxazol-4-yl)-2-[1,2,3]triazol-2-yl-oct-6-en-4-ynoic acid;

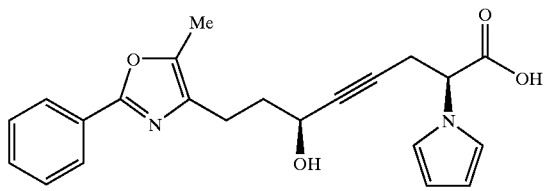

6-Hydroxy-8-(5-methyl-2-phenyl-oxazol-4-yl)-2-pyrrol-1-yl-oct-4-ynoic acid;

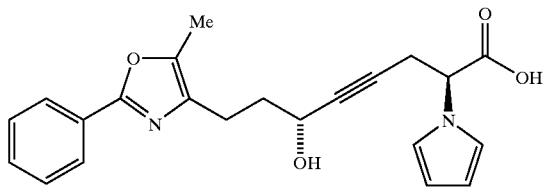

6-Methoxy-8-(5-methyl-2-phenyl-oxazol-4-yl)-2-pyrrol-1-yl-oct-4-ynoic acid;

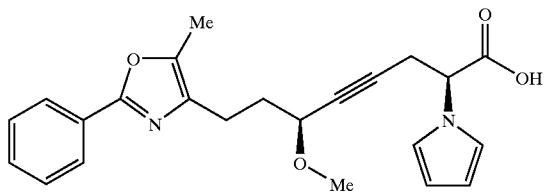

6-Methoxy-8-(5-methyl-2-phenyl-oxazol-4-yl)-2-pyrrol1-yl-oct-4-ynoic acid;

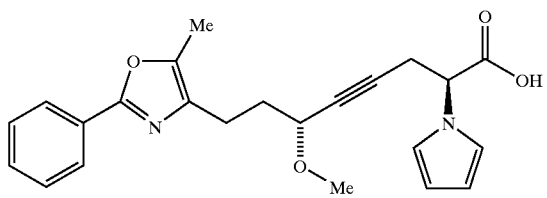

6-Methoxy-8-(5-methyl-2-phenyl-oxazol-4-yl)-2-pyrrol1-yl-oct-4-ynoic acid;

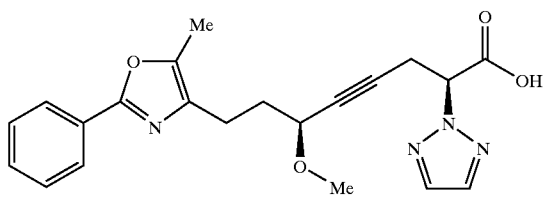

6-Methoxy-8-(5-methyl-2-phenyl-oxazol-4-yl)-2-[1,2,3]triazol-2-yl-oct-4-ynoic acid; or

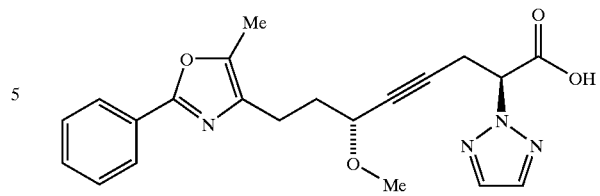

6-Methoxy-8-(5-methyl-2-phenyl-oxazol-4-yl)-2-[1,2,3]triazol-2-yl-oct-4-ynoic acid.

11. A pharmaceutical composition comprising a compound of claim 1 admixed with a carrier, diluent, or excipient.

12. A method of treating, non-insulin dependent diabetes mellitus, obesity, hyperglycemia, hyperlipidemia, hypercholesteremia, atherosclerosis, hypertriglyceridemia, hyperinsulinemia in a mammal comprising administering to the mammal in need thereof an effective amount of a compound of claim 1.

13. A method of treating a patient suffering from abnormal insulin and/or evidence of glucose disorders associated with circulating glucocorticoids, growth hormone, catecholamines, glucagon, or parathyroid hormone, or of reducing body weight in an obese patient, comprising administering to the patient a therapeutically effective amount of a compound of fomula I.

14. A a method of preparing a compound of formula IA

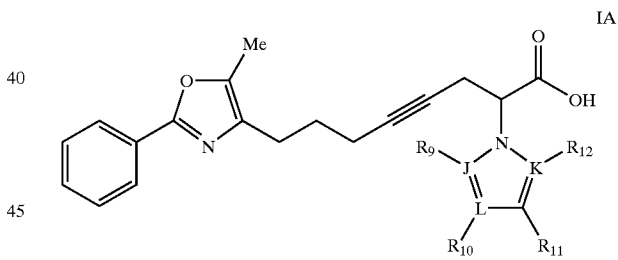

IA wherein $R_9$–$R_{12}$ are each independently H, halo, aryl, $(C_1$–$C_6)$alkyl, halo$(C_1$–$C_6)$alkyl, $(C_1$–$C_6)$alkanoyl, halo$(C_1$–$C_6)$alkanoyl, $(C_3$–$C_7)$cycloalkylcarbonyl, benzoyl, or halo$(C_2$–$C_6)$alkanoyl; and one, two, or three of J, K, and L are N, provided that when J, K, or L are N, $R_9$, $R_{10}$, and $R_{12}$ are absent at that position comprising:

(a) Conversion of the mesylate to the nitrile;

(j) Conversion of the nitrile to the primary alcohol;

(k) Conversion of the primary alcohol to the halide;

(l) Displacement of the halide with TMSacetylide to to form the TMS acetylene;

(m) Removal of the TMS group by hydrolysis;

(n) Treatment of the acetylene with base and reaction with formaldehyde to form the propargyl alcohol;

(o) Conversion of the primary alcohol to the Halde;

(p) Alkylation with "X" follwed by decarboxylation to form the ester;
(q) Hydrolysis of the ester:

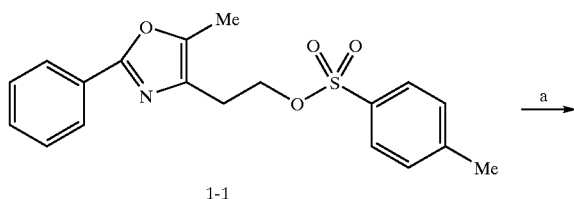

1-1

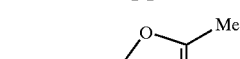

1-2

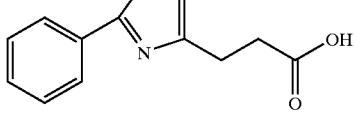

1-3

1-4

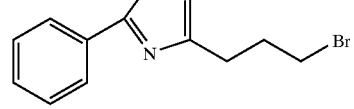

1-5

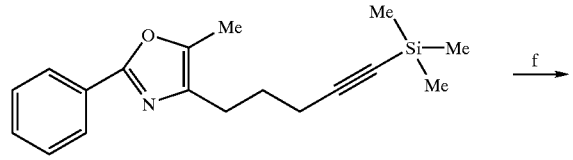

1-6

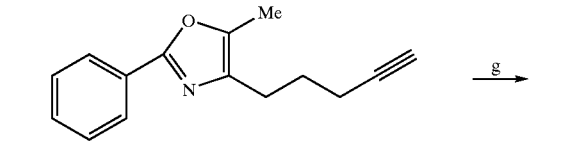

1-7

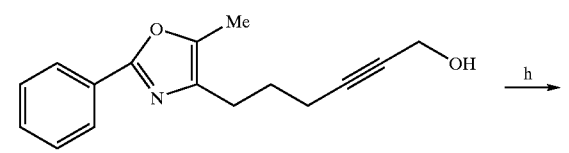

1-8

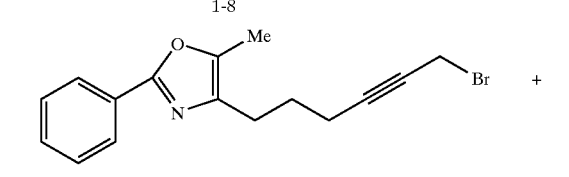

1-9

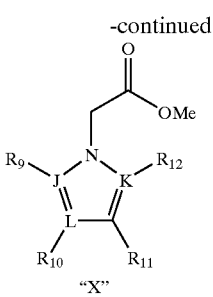

"X"

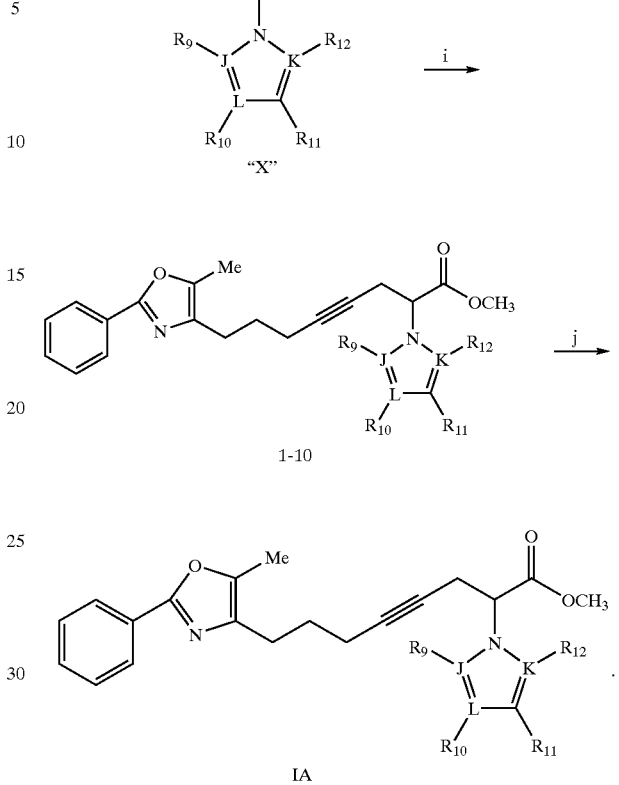

1-10

IA

15. A method of preparing a compound of formula IB

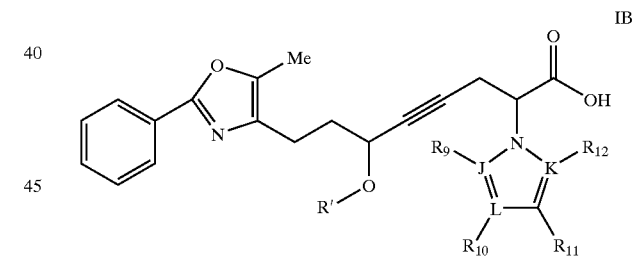

IB wherein R' is H, $(C_1-C_6)$alkyl;

$R_9-R_{12}$ are independently H, halo, aryl, $(C_1-C_6)$alkyl, halo$(C_1-C_6)$alkyl, $(C_1-C_6)$alkanoyl, halo$(C_1-C_6)$alkanoyl, benzoyl, or halo$(C_2-C_6)$alkanoyl; and one, two, or three of J, K, and L are N, provided that when J, K, or L are N, $R_9$, $R_{10}$, and $R_{12}$ are absent at that position comprising: